US012773472B2

(12) United States Patent
Weindl et al.

(10) Patent No.: US 12,773,472 B2
(45) Date of Patent: Oct. 27, 2026

(54) HEMOSTATIC MATERIALS BASED ON ALDEHYDE-FUNCTIONAL POLYSACCHARIDES

(71) Applicant: Ethicon, Inc., Raritan, NJ (US)

(72) Inventors: Thomas Weindl, Raritan, NJ (US); Benjamin Fitz, Raritan, NJ (US); Gaojie Hu, Raritan, NJ (US)

(73) Assignee: Ethicon, Inc., Raritan, NJ (US)

( * ) Notice: Subject to any disclaimer, the term of this patent is extended or adjusted under 35 U.S.C. 154(b) by 515 days.

(21) Appl. No.: 18/358,109

(22) Filed: Jul. 25, 2023

(65) Prior Publication Data

US 2025/0032666 A1 Jan. 30, 2025

(51) Int. Cl.
*A61L 24/08* (2006.01)

(52) U.S. Cl.
CPC ........... *A61L 24/08* (2013.01); *A61L 2400/04* (2013.01); *A61L 2400/06* (2013.01)

(58) Field of Classification Search
CPC .. A61L 24/08; A61L 2400/04; A61L 2400/06; A61L 15/28
See application file for complete search history.

(56) References Cited

U.S. PATENT DOCUMENTS

| | | | |
|---|---|---|---|
| 6,165,488 | A | 12/2000 | Tardy et al. |
| 7,252,837 | B2 | 8/2007 | Guo et al. |
| 7,589,051 | B2 | 9/2009 | Erazo-Majewicz et al. |
| 8,241,609 | B2 | 8/2012 | Figuly et al. |
| 8,426,492 | B2 | 4/2013 | Lu |
| 8,551,136 | B2 | 10/2013 | Lu |
| 8,715,636 | B2 | 5/2014 | Kodokian et al. |
| 8,951,989 | B2 | 2/2015 | Wagman |
| 10,376,610 | B2 | 8/2019 | Ertan |
| 10,420,794 | B2 | 9/2019 | Medina et al. |
| 2006/0134185 | A1 | 6/2006 | Odermatt et al. |
| 2006/0159733 | A1 | 7/2006 | Pendharkar et al. |
| 2007/0104660 | A1* | 5/2007 | Miksa ...................... A61K 8/11 424/49 |
| 2008/0207894 | A1 | 8/2008 | Trksak |
| 2012/0148523 | A1 | 6/2012 | Lu et al. |
| 2016/0317703 | A1 | 11/2016 | Wuollett et al. |
| 2018/0117019 | A1* | 5/2018 | Wang ..................... A61K 47/32 |
| 2020/0352982 | A1* | 11/2020 | Laas .................... A61K 31/718 |
| 2022/0096708 | A1 | 3/2022 | Chen et al. |
| 2022/0202619 | A1 | 6/2022 | Feng et al. |

FOREIGN PATENT DOCUMENTS

| | | | |
|---|---|---|---|
| CN | 101632685 | B | 7/2012 |
| CN | 105530997 | A | 4/2016 |
| CN | 110917385 | A | 3/2020 |
| CN | 111905141 | A | 11/2020 |
| CN | 111921004 | A | 11/2020 |
| EP | 0815879 | | 1/1998 |
| EP | 1438079 | B1 | 4/2005 |
| JP | 2017202033 | A | 11/2017 |
| KR | 102442102 | B1 | 9/2022 |

OTHER PUBLICATIONS

Plappert, et al., Transparent, Flexible, and Strong 2,3-Dialdehyde Cellulose Films with High Oxygen Barrier Properties, Biomacromolecules, 2018, pp. 2969-2978, vol. 19.
International Search Report and Written Opinion, received for PCT Application No. PCT/IB2024/057171, mailed on Dec. 5, 2024, 15 pages.
Invitation to Pay Additional Fees, received for PCT Application No. PCT/IB2024/057171, mailed on Oct. 7, 2024, 2 pages.

* cited by examiner

Primary Examiner — David Browe
(74) *Attorney, Agent, or Firm* — David R. Crichton; Leo B. Kriksunov

(57) ABSTRACT

The present invention is directed to hemostatic and/or tissue adhesive formulations comprising crosslinked polysaccharide particles that have been oxidized to generate aldehyde- and carboxylic functional moieties therein, and wherein said formulations further contain a buffer that maintains a slightly alkaline environment. These formulations can be applied onto tissue in the form of a powder, paste or patch to effect hemostasis or sealing.

6 Claims, 1 Drawing Sheet

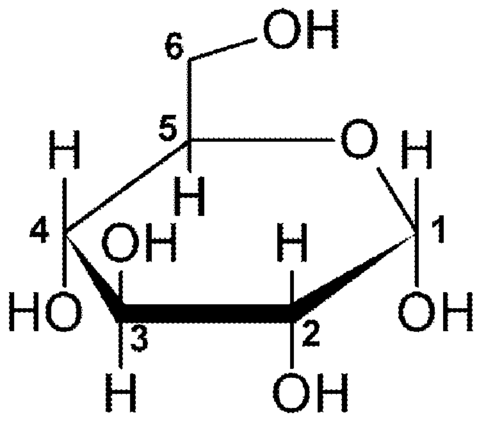
Glucose

HEMOSTATIC MATERIALS BASED ON ALDEHYDE-FUNCTIONAL POLYSACCHARIDES

FIELD OF THE INVENTION

This invention relates to hemostatic/sealing formulations comprising crosslinked polysaccharide particles that have been oxidized to generate aldehyde-functional moieties therein, and wherein said formulations further contain a buffer that maintains a slightly alkaline environment. These formulations can be applied onto tissue in the form of a powder, paste or patch to effect hemostasis or sealing.

BACKGROUND OF THE INVENTION

Adjunctive hemostatic agents have taken many forms, the most common being woven and nonwoven oxidized-cellulose matrices such as SURGICEL® Original, NuKnit, SNoW, etc. The efficacy of a hemostatic material in matrix format is typically augmented by the ability to apply tamponade. Similar challenges are observed in flowable formats of hemostatic matrix products, such as SURGIFLO® derived from SURGIFOAM®, where sufficient hemostasis is typically achieved through the addition of a biological clot-forming agent, thrombin, rather than through the material properties alone. When blood is heparinized, the challenge in achieving hemostasis for most non-augmented approaches becomes insurmountable.

European patent application EP 815 879 describes a bioabsorbable material which, from oxidized polysaccharides, can be used in the form of a freeze-dried sponge for hemostasis and for avoiding adhesion in surgical interventions. The bioabsorbable material consists of a water-soluble cellulose derivative which has primary alcohol groups in the range of 3 to 12% oxidized to the carboxylic acid.

U.S. Pat. No. 7,252,837 relates to hemostatic wound dressings, more specifically, a flexible hemostatic patch comprising a knitted fabric of oxidized cellulose and a porous water-soluble or water-swellable polymeric matrix, and to a process of making such fabrics and wound dressings. With regard to the process, U.S. '837 describes processes for making a wound dressing for use with moderate to severe bleeding, the wound dressing comprising a fabric that comprises oxidized regenerated cellulose fibers and a biocompatible, water-soluble or water-swellable polymer matrix of sodium carboxymethyl cellulose, the process consisting of the steps of: providing a solution having dissolved therein sodium carboxymethyl cellulose, providing a fabric having a top surface and a bottom surface opposing said top surface, said fabric having flexibility, strength and porosity effective for use as a hemostat, immersing said fabric at least partially in said solution to distribute said solution at least partially through said fibers, lyophilizing said fabric and said solution distributed at least partially through said fibers, thereby forming a porous polymeric matrix at least partially integrated with or about the fibers having a microporous structure with a large fluid absorbing capacity.

US Publication No. 2006/0134185A1 describes resorbable hemostyptic that is self-adhering to human or animal tissue and essentially consisting of at least one polymer which carries free aldehyde groups and whose aldehyde groups are able to react with nucleophilic groups of the tissue, the hemostyptic being present in solid, dry, porous and absorbent form, to a method for its production. In one embodiment therein, the polymer carrying aldehyde groups is oxidized, in particular bioabsorbable polysaccharide, such as dextran polyaldehyde. The proportion of glucose units oxidized to the aldehyde in the dextran polyaldehyde can be at least 20%, preferably 35-100%, in particular between 60 and 80%. In certain embodiments, the polymer carrying aldehyde groups is partially cross-linked, before use, with a cross-linking agent, preferably chitosan. Dextran polyaldehyde is a type of modified dextran, which is a complex carbohydrate made up of glucose molecules. In dextran polyaldehyde, some of the glucose molecules have been chemically modified to contain an aldehyde group.

U.S. Pat. No. 8,426,492 describes tissue adhesive formed by reacting an oxidized cationic polysaccharide containing aldehyde groups and amine groups with a multi-arm amine. U.S. '492 indicates that the oxidized polysaccharide containing aldehyde groups and amine groups is derived from a polysaccharide selected from the group consisting of dextran, carboxymethyl dextran, starch, agar, cellulose, hydroxyethyl cellulose, carboxymethyl cellulose, pullulan, inulun, levan, agarose, and hyaluronic acid. In one embodiment, the oxidized polysaccharide containing aldehyde groups and amine groups is oxidized diethylaminoethyl dextran or oxidized aminated dextran.

SUMMARY OF THE INVENTION

The present invention is, in one embodiment, directed to materials in powder form comprising a periodate oxidized and starch glycolate or carboxy methyl starch, which can be used directly as powder or extruded as a small fiber, wherein said materials further contain an alkaline buffer that is provided prior to application onto tissue. The powder form can be sprayed onto a bloody surface to achieve hemostasis with or without the use of tamponade.

In an alternative embodiment, the present invention is a flowable material comprising periodate oxidized and starch glycolate or carboxy methyl starch that has been partially hydrated with water or partially wetted with a binder such as glycerol to form a paste, wherein said materials further contain an alkaline buffer prior to application onto tissue.

In an alternative embodiment, the present invention is a wound dressing in the form of a patch or sponge containing periodate oxidized sodium starch glycolate that can be applied directly a bleeding site to achieve hemostasis. The patches, in woven or non-woven form, can be generated through fiber extrusion or spinning of the periodate oxidized sodium starch glycolate and subsequent weaving or entanglement in known fashion.

The preceding materials and formulations can be combined within substrates and carriers for purposes of application onto a tissue surface.

BRIEF DESCRIPTION OF THE DRAWINGS

FIG. 1 is a molecular drawing to illustrate the structure of glucose.

DETAILED DESCRIPTION OF INVENTION

The hemostatic/sealing formulations of the present invention adhere to tissue as a result of oxidized polysaccharides, such as crosslinked starch glycolate, crosslinked carboxymethyl starch or carboxymethyl cellulose particles that have been further oxidized to form aldehyde-functional moieties, wherein said formulations further contain an alkaline buffer.

These formulations can be applied onto tissue in the form of a powder, paste or from a particle containing patch to effect hemostasis or sealing.

The inventors have discovered that an aldehyde-functionalized form of a polysaccharide, preferably a crosslinked sodium starch glycolate that has been oxidized post-crosslinking, is capable of crosslinking with blood and tissue surfaces to achieve hemostasis of heavily heparinized blood, particularly when combined with a buffering agent. This aldehyde-functionalized material can be spun into a fiber to produce matrices, used directly as a powder, or partially wetted and delivered as a flowable product. The material can optionally be fully dissolved and applied in liquid form in conjunction with a reactive polyamine to achieve hemostasis.

A polysaccharide is a type of carbohydrate that is composed of many sugar units (typically glucose) linked together. Glucose comes in the form α or β depending on the orientation of the hydroxyl group at position 1 (see FIGURE). Starch is composed of two kinds of α-glucose: amylose (linear or slightly branched with units linked at position 1 and 4, with degree of polymerization (Dp) up to 6,000) and amylopectin (branched with additional links at position 1 and 6 with a Dp up to 2,000,000).

Potato starch contains approximately 21% amylose and 79% amylopectin. Corn starch contains approximately 25-30% amylose and 70-75% amylpectin. Amylose is a linear polymer of glucose units connected by alpha-1,4-glycosidic bonds that forms a helical structure and is responsible for the formation of a gel when starch is heated in water. Amylpectin, on the other hand, is a highly branched polymer of glucose units connected by both alpha-1,4-glycosidic bonds (similar to amylose) and alpha-1,6-glycosidic bonds, which introduce branching points. Amylpectin provides the structural framework for starch granules.

Polysaccharides can be linear or branched, and they can be classified based on their chemical structure. Examples of polysaccharides include starch, cellulose, glycogen and dextran. Starch is a polysaccharide that is composed of glucose molecules and is found in plants. Dextran, on the other hand, is a complex carbohydrate that is composed of a chain of glucose molecules. Complex carbohydrate is a more general term that refers to any carbohydrate that is made up of multiple sugar units, which includes not only polysaccharides but also disaccharides and oligosaccharides, which are made up of two or a few sugar units respectively. Dextran is produced by certain types of bacteria and can be found in various forms such as solutions, gels and powders. Dextran is more water-soluble than starch.

Polysaccharide Materials

Starch

Starch glycolate is a modified form of starch that has been treated with glycolic acid. This modification increases the solubility and stability of the starch, making it useful in a variety of applications such as food and pharmaceuticals. It is also used as a disintegrant in tablets and capsules. Starch glycolate is often used as a binder, thickener and disintegrant in solid dosage forms. Sodium starch glycolate is the sodium salt of carboxymethyl ether. Sources of starch glycolates are rice, potato, wheat or corn. Sodium starch glycolate is a commonly used super-disintegrant. Sodium starch glycolate is manufactured by chemical modification of starch, i.e., carboxymethylation to enhance hydrophilicity and crosslinking to reduce solubility.

The European Pharmacopoeia and USP/NF differentiate sodium starch glycolate Types A, B and C as summarized in Table 1.

TABLE 1

Properties of sodium starch glycolate.

| Test | Type A | Type B | Type C |
|---|---|---|---|
| pH | 5.5-7.5 | 3.0-5.0 | 5.5-7.5 |
| NaCl | Max 7% | Max 7% | Max 1% |
| LOD | Max 10% | Max 10% | Max 7% |
| Assay Na | 2.8%-4.2% | 2.0%-3.4% | 2.8%-5.0% |

The preferred form of sodium starch glycolate for use in the formulations of the present invention falls within the scope of the monograph for Type A.

Starch glycolate can be found in both powder and granule form. The powder form of starch glycolate is a fine, white powder that is easy to handle and can be easily dissolved in water or other solvents. The powder form is often used in applications such as food and pharmaceuticals as a thickener, binder, and disintegrant in solid dosage forms. The granule form of starch glycolate is also available The granular form is made by granulating the powder form of starch glycolate. The customary size of starch glycolate in granular form can vary depending on the specific application and desired properties. However, in general, the granules are usually between 100-250 micrometers (μm) in diameter. The granule size can be adjusted through a process called granulation. This process involves the formation of small particles into larger granules, the size can be controlled by adjusting the granulation parameters such as the binder solution concentration, granulation time, and granulation speed. Larger granules will have a lower swelling capacity and surface area, while smaller granules will have a higher swelling capacity and surface area.

Carboxymethyl starch (CMS) is a modified form of starch in which some of the hydroxyl groups of the starch molecules have been converted to carboxymethyl groups. This modification process increases the stability and water-solubility of the starch. CMS is typically produced by chemically modifying starch using the process of carboxymethylation through reaction of starch with sodium monochloroacetate (SMCA) in the presence of an alkali, such as sodium hydroxide. The reaction is typically carried out at a high temperature (around 80-90 degrees Celsius) and under high pressure. The degree of substitution (DS) of the resulting CMS can be controlled by varying the amount of SMCA used and the reaction time.

One example of a polysaccharide is sodium starch glycolate that commercially available as a super disintegrant Primojel®, which is generally prepared from a crosslinked potato starch. The resulting starch powder is then mixed with water and an enzyme, such as alpha-amylase, to partially hydrolyze the starch to break down the starch molecules into smaller fragments, creating a mixture of starch fragments and glucose. As noted above, potato starch contains approximately 21% amylose and 79% amylpectin. When potato starch undergoes hydrolysis using an enzyme like alpha-amylase, it breaks down the starch molecules into smaller components through the cleavage of glycosidic bonds. Alpha-amylase specifically acts on the alpha-1,4-glycosidic bonds in starch, which are the primary linkages in both amylose and amylpectin. The hydrolysis of potato starch by alpha-amylase produces a mixture of shorter polysaccharides, oligosaccharides, and ultimately glucose units. The resulting mixture of products from the hydrolysis of corn starch by alpha-amylase typically contains glucose, maltose, maltotriose, and various shorter oligosaccharides.

Carboxymethyl cellulose (CMC) is a cellulose derivative that has carboxymethyl groups (—CH2COOH) substituted onto the hydroxyl groups of the cellulose molecule. Cellulose is the primary raw material for the production of carboxymethyl cellulose (CMC). The sources of cellulose for CMC production include wood pulp, cotton linter; Bagasse, a byproduct of the sugar cane industry; and straw from crops such as wheat, rice, and corn. The production of carboxymethyl cellulose (CMC) from cellulose involves the substitution of carboxymethyl groups onto the hydroxyl groups of the cellulose molecule.

Cross-Linking of Polysaccharides

Polysaccharides, such as sodium starch glycolate (SSG), CMS, can be crosslinked through a variety of methods, such as crosslinking with chemical agents using agents such as epichlorohydrin, which reacts with the hydroxyl groups on the starch molecules to form covalent bonds; with heat and pressure by heating and pressing the starch components, which causes the starch molecules to form hydrogen bonds with each other; with enzymes by treating the starch components with enzymes such as transglutaminase, which catalyzes the formation of covalent bonds between the starch molecules; and with ionizing radiation by exposing the starch component to ionizing radiation, which causes the formation of chemical bonds between the starch molecules.

The partially hydrolyzed starch used to make starch glycolate can be mixed with a solution of sodium hydroxide and glycolic acid to crosslink the starch fragments and to form a gel-like substance. The gel is then dried to remove any remaining water and reduce the overall moisture content. The resulting dry powder is then screened to remove any impurities.

Another means for modifying the properties of polysaccharides is to form internal crosslinking network via phosphate crosslinking. Phosphate crosslinking is a process in which phosphoric acid or a phosphorous-containing compound is used to create covalent bonds between the starch molecules. For example, potato starch can be crosslinked using sodium trimetaphosphate or phosphorus oxychloride in alkaline suspension.

The process of phosphate crosslinking of polysaccharides typically involves the following steps: dissolve the polysaccharide, such as potato starch, in water or a suitable solvent; add a phosphorous-containing compound, such as orthophosphoric acid, to the solution and mix well, the concentration and reaction time will depend on the desired degree of crosslinking; allow the mixture to react for a certain period of time; neutralize the reaction mixture with a suitable neutralizing agent, such as sodium hydroxide; and wash the crosslinked starch to remove any remaining phosphorous-containing compound and neutralizing agent.

The cross linked potato starch described above can be further substituted using chloroacetic acid or sodium monochloroacetate in an alkaline alcoholic suspension according to Williamson's ether synthesis to replace at least some of the available hydroxy groups in the anhydroglucose units of the starch units. In a preferred embodiment, one (1) AGU in every four (4) units is substituted with a carboxylmethyl group.

Oxidation Processing

Crosslinked SSG, which is preferably at least partially substituted with carboxymethyl groups, as described above can be further oxidized using sodium periodate to yield aldehyde-functionality in the remaining hydroxy groups. Sodium periodate ($NaIO_4$) reacts with SSG, specifically targeting the vicinal diols (adjacent hydroxyl groups) present in the starch molecule. The periodate ion (IO4-) cleaves the C—C bond between the two adjacent hydroxyl groups, forming aldehydes (CHO, preferred), aldehyde/ketone and/or carboxylic acid groups and generating an intermediate compound. The intermediate compound formed in the activation step undergoes a rearrangement, resulting in the formation of aldehyde starch. The rearrangement involves the migration of some of the oxygen atoms to create two aldehyde groups on the starch molecule. The resulting aldehyde starch (also referred to as aldehyde starch or periodate-oxidized starch) contains aldehyde functional groups (—CHO) along the starch chain. If starch glycolate is oxidized with periodate, the resulting product will typically be a white powder or granules, depending on the starting form.

These modified polysaccharide compounds that have been crosslinked and substituted, as least in part, will now have aldehyde groups that are chemically reactive and can participate in various reactions such as cross-linking or conjugation with other molecules containing amine or hydrazine groups. The presence of aldehyde functional groups allows the material to crosslink directly with amines present in blood and on the tissue surface. The resulting aldehyde groups on the starch/carbohydrate molecules can react with other starch molecules to form covalent cross-links. This process is also known as periodate oxidation crosslinking.

The oxidation process can be controlled to produce SSC, CMS or CMC with varying degrees of oxidation and aldehyde content, depending on the conditions used.

Lyophilization of Aldehyde Functionalized and Crosslinked Polysaccharides

Lyophilization, also known as freeze-drying, is a process in which water is removed from a product through sublimation (the transition of a substance from a solid to a gas without passing through a liquid phase). In the case of starch particles, the process typically involves the following steps: Starch particles are suspended in a liquid, typically water or a water-based solution; the suspension is then frozen, typically at temperatures between −20° C. and −80° C.; the frozen suspension is placed under a vacuum, which causes the ice to sublimate (i.e., change from a solid to a gas) and be removed from the starch particles; once the majority of the ice has been removed, the temperature is slowly raised to higher temperature, which causes any remaining ice to sublimate and the product to be dried. The lyophilized starch particles are then packaged and stored until they are ready to be used.

The preferred lyophilization conditions for the inventive hemostatic formulations are: Stepwise shelf lyophilization at −20° C., −10° C., 0° C., 10° C. to 5° C. or 20° C. For aldehydes embedded with basic buffer, the highest shelf temperature for lyophilization was 5° C. to prevent undesired cross-linking reaction at elevated temperature for prolonged time.

The resulting lyophilized granules are characterized by titration to determine oxidation degree and when soluble by GPC to determine molecular weight. NMR can also be used for aldehyde and AGU determination. However, these compounds typically form complex and dynamic structures to provide straightforward and accurate data interpretation (reference: Transparent, Flexible, and Strong 2,3-Dialdehyde Cellulose Films with High Oxygen Barrier Properties, Biomacromolecules, 2018, 19 (7), 2969-2978).

Buffering Agents

Buffers are materials that can help to maintain a stable pH level in a solution when an acidic or basic substance is added to it. Buffers include but not limited to bicarbonate, carbonate, phosphates, citrate, acetate, borate, imidazole, pyridine, ammonium, formate and zwitterionic buffers. A zwitterionic buffering agent is a molecule that has both a positive and a negative charge within the same molecule, allowing it to act as a buffer over a wide range of pH values. A few examples of zwitterionic buffering agents include: Tris(Hydroxymethyl)aminomethane (Tris), which has a pKa of 8.1 and is able to buffer in the pH range of 7.5-9.1; MOPS (3-(N-Morpholino) propanesulfonic acid), which has a pKa of 7.2 and is able to buffer in the pH range of 6.5-7.9; CHES (2-(Cyclohexylamino)ethanesulfonic acid), which has a pKa of 9.5 and is able to buffer in the pH range of 8.6-10.0; MES (2-(N-Morpholino)ethanesulfonic acid), which has a pKa of 6.1; and PIPES (piperazine-N,N'-bis(2-ethanesulfonic acid)), which has a pKa of 6.8; and Bis-Tris(bis(2hydroxyethyl)iminotris-(hydroxymethyl)methane), which has a pKa of 6.5 and 6.9.

A preferred buffer for these formulations is 2-(cyclohexylamino)ethanesulfonate (CHES) that is combined with the crosslinked and oxidized polysaccharides described above in the form of a powder blend, or with nucleophilic agent in the form of aqueous dispersion. The blended weight ratio of buffering agent to starch granules is selected to achieve hemostasis or sealing within two (2) minutes of initiating in-vivo curing (cross-linking of aldehydes with biologic or synthetic nucleophilic component) and depends on severity of bleeding or leakage and formulation details (if external nucleophilic components are provided in addition to amines from biologic sources including body fluids and tissues).

Lyophilization in the Presence of Buffering Agents

In one embodiment, a preferred buffering agent is derived from a CHES-containing solution that has been lyophilized with the oxidized and crosslinked polysaccharides. The lyophilization process and operation conditions will depend on various factors, such as the concentration of the solution, the presence of other ingredients, and the desired outcome of the lyophilization process. Customary lyophilization conditions for CHES solutions include:

a) Add aldehyde functionalized component (solid) to pH adjusted CHES solution to fully dissolved at ambient temperatures.
b) Alternatively, add CHES (solid) to a aldehyde functionalized component containing solution (purified but un-lyophilized from oxidation reaction) to full dissolution and then adjust the pH to the desired range.
c) Freeze the composite solution prepared in (a) or (b) at a controlled rate, usually at −20° C. to −80° C., to minimize damage to the active ingredients;
d) Apply a vacuum to the frozen solution to remove the water at a pressure of 100 mTorr or less;
e) Ramp the temperature of the solution slowly from the freeze temperature to 5° C. to allow the remaining water to sublime; and
f) Seal the dried powder in a moisture-proof container to prevent rehydration.

A preferred lyophilization process proceeds by (b) for leaner processing step without having to lyophilize the aldehyde to solids. A preferred lyophilization process produces an oxidized, crosslinked aldehyde functionalized compound with a CHES-buffer as a lyophilizate in the form of solids.

Fillers

The formulations described above can be further modified by additions of chitosan and/or nanocellulose. Chitosan is a biopolymer that is derived from chitin, a natural polymer found in the shells of crustaceans such as shrimp and crabs. Chitosan is produced by deacetylation of chitin, which results in a positively charged, water-soluble polymer with unique physical and chemical properties.

Nanocellulose can be produced through various methods, including mechanical, chemical, and enzymatic processes starting from a cellulose-rich plant material, such as wood pulp, bamboo, cotton, sisal, kenaf, tunicate cellulose, bacteria or other cellulosic sources. These materials are prepared on a nanoscale to preferably form nanofibrils or nanocrystals.

Product Forms

In one embodiment, the present invention is a material in powder form comprising a periodate oxidized sodium starch glycolate or CMS, which can be used directly as powder or extruded as a small fiber. The powder form, when combined with a buffering agent, can be sprayed onto a bloody surface to achieve hemostasis with or without the use of tamponade.

In an alternative embodiment, the present invention is a flowable material comprising periodate oxidized sodium starch glycolate or CMS that has been partially hydrated with water or partially wetted with a binder such as glycerol to form a paste. The paste can be stored as-is and, once combined with a buffering agent, and upon injection into a moist tissue surface will achieve hemostasis with or without tamponade. The flowable material can be combined with other active agents as needed.

In an alternative embodiment, the present invention is a wound dressing in the form of a patch or sponge containing periodate oxidized sodium starch glycolate or CMS, once combined with the buffering agent, which can be applied directly onto a moist tissue or bleeding site to achieve hemostasis and/or sealing. The patches, in woven or non-woven form, can be generated through fiber extrusion or spinning of the periodate oxidized sodium starch glycolate and subsequent weaving or entanglement in known fashion.

The swellable nature of the resulting materials allow for high reactivity and hemostatic functionality in the presence of blood. For full functionality, the system can utilize either a dry or wet buffer that can be incorporated through: (a) pre-mixing or internally embedding within the polyaldehyde functionalized starch as a matrix and activated upon wetting (such as by saline, blood, physiological fluids, etc.); or (b) integration only at the time of use, such with separately containers and a mixing element. Upon activation, the matrix pH is neutral to basic, preferably basic.

These formulations exhibit improved adherence to tissue and hemostatic activity relative to the non-oxidized particles and/or relative to oxidized particles that lack the buffer component. Further, addition of these particles onto or in combination with substrates enhances hemostatic efficacy. The substrates can be either in the form of patch, pad or powders. In certain embodiments, the particles have been lyophilized. In certain embodiments, the substrates are cellulosic. In alternative embodiments, the cellulosic substrates have been lyophilized before addition of the starch particles or after addition of the starch particles. Dried sponges can be generated through partial hydration and subsequent lyophilization.

In one embodiment, the present invention is a hemostatic/sealing and tissue adhesive material comprising:

a) a crosslinked starch glycolate or carboxymethyl starch that has been oxidized, such as via a periodate oxidation, to form a plurality of aldehyde-functional moieties;
b) a zwitteronic buffer that is provided prior to application onto tissue, wherein said material used as a powder, paste, patch or dried sponge that can be applied onto tissue to effect hemostasis or sealing.

In an alternative embodiment, the present invention is a hemostatic/sealing and tissue adhesive material as described above that is in the form of a powder distributed or applied onto a substrate material. The substrate materials can be woven, non-woven or porous sponge material constructed from CMC or oxidized cellulose. The powder on substrate is preferably applied, but not fixated, in the amount of about 5-70 mg of material per square centimeter of an applied surface area of the substrate, preferably 20-50 mg/cm$^2$. The hemostatic, sealing and/or adhesive material can be applied on the substrate and then lyophilized to produce a final form as a lyophilized wound dressing.

Methods of Application

In one embodiment, there is a method for coating an anatomical site on tissue of a living organism comprising: applying to the site a) at least one oxidized polysaccharide containing aldehyde groups, followed by b) at least one buffering agent and, optionally, c) a water-dispersible, multi-arm amine wherein at least three of the arms are terminated by a primary amine group; or alternatively, applying (b) followed by (a) or (c) and mixing (a) and (b) or (c) on the site, or alternatively, premixing (a) and (b) and optionally (c) applying the resulting mixture to the site.

Another embodiment provides the method, wherein the oxidized polysaccharide is a first aqueous solution or dispersion and the buffer is in a second aqueous solution or dispersion.

In yet another embodiment, the method, wherein the oxidized polysaccharide, buffer and optionally the multi-arm amine are finely divided powders.

In yet another embodiment, the method, wherein the oxidized polysaccharide, buffer and optionally the multi-arm amine are incorporated onto a carrier, patch, pad or substrate.

In yet another embodiment, the method, wherein the oxidized polysaccharide is oxidized CMS or oxidized starch glycolate and the multi-arm amine is a multi-arm polyethylene glycol amine.

The following examples are illustrative of the principles and practice of the present invention, although not limited thereto. Numerous additional embodiments within the scope and spirit of the invention will become apparent to those skilled in the art once having the benefit of this disclosure.

EXAMPLES

Example 1—Powder Application of Unoxidized and Periodate Oxidized Sodium Starch Glycolate (POSSG) with Buffer (CHES)

1.1 Starting Materials: Sodium Starch Glycolate

Sodium starch glycolate that has been cross-linked and is commercially available as general chemical reagents, also under tradenames including Primojel® (DFE Pharma), GLYCOLYS® (ROQEUTTE) and EXPLOTAB® (JRS Pharma).

1.2 Sodium Starch Glycolate Oxidation

To a 500 mL Erlenmeyer flask with 400 mL DI water (0.31 M) was added 20.01 grams (0.124 mol) of crosslinked sodium starch glycolate (Primojel®) with magnetic stirring at room temperature. Once the powder was fully dispensed to form a white translucent solution, 26.41 grams (1.0 molar equiv.) of sodium (meta)periodate was added to the solution portion-wise. The whole reaction vessel was then fully wrapped with alumina foil to shield from light. The reaction solution was continued stirring at room temperature for 18 hours. The solution was then quenched with 5 mL ethylene glycol. The quench reaction continued in dark at room temperature for another 5 hours. The oxidized sodium starch glycolate was purified via dialysis against DI water for 3 days using Mw 3.5K cutoff membrane (with multiple water replacement in between). The purified solution was lyophilized via a stepwise setup from −20 to 20° C. (shelf temperature) to give 12.81 grams (64% yield) of white powdery solids as the sodium starch glycolate aldehyde.

1.3 Aldehyde Oxidation Degree by Titration

For oxidation degree determination, 194.6 mg (0.15-0.2 grams for this method in general) aldehyde was added to 10.00 mL 0.25 N aq. NaOH solution in a 125 mL Erlenmeyer flask at 70° C. with gentle swirling for 2 min. The reaction flask was then rapidly cooled under running tap water for 1 min. 15.00 mL 0.25 N aq. HCl, 50 mL DI water and 1.00 mL 0.2% phenolphthalein (prepared by mixing 16 mL DI water with 4 mL 1% phenolphthalein in ethanol—commercial solution) was added to the reaction flask. The combined solution was titrated using 0.25 N aq. NaOH until the solution turns slightly pink as the end point. In this case, it consumed 7.09 mL aq. NaOH in titration. % Oxidation degree was calculated using the following equation:

% Oxidation=[(Titration Consumption Volume−15.00+10.00)*0.25]/[mass of aldehyde/starch AGU Mw].

Starch AGU molecular weight was assumed 162. The calculated oxidation degree was 43.2% for the materials produced in Example 1.

1.4 Composite Powder of Oxidized Sodium Starch Glycolate with Buffer

To 90 mL DI water was added 4.14 grams of CHES (0.2 M) at room temperature. The pH of the clear solution was adjusted with aq. NaOH to 9.65. 4.01 grams of oxidized sodium starch glycolate was added to the buffer solution to form a slightly translucent solution, which was lyophilized via a stepwise setup from −20 to 5° C. (shelf temperature) to give 7.31 grams of white powder as the composite powder product. The fed CHES (Mw 207.29) is 0.81 molar equiv. of starch AGU (Mw 162). In the lowered CHES buffer case, 0.17 molar equiv. of CHES over starch AGU was added in the initial solution preparation. In the case with sodium bicarbonate buffer in the composite powder, sodium bicarbonate powder was used instead of CHES (0.87 molar equiv. of starch AGU).

Performance Tests

Performance testing was performed using sodium starch glycolate (Primojel®) as described in the Starting Material in Example 1, both as non-oxidized and oxidized as shown in Example 1.2, in contact with non-clotting heparinized blood: Bovine whole blood with added as Na-Heparin (1000 units of heparin per 100 mL blood). Testing was performed by adding powder of sodium starch glycolate, in the non-oxidized and oxidized forms, to a vial containing whole blood (NN ml of blood in the vial) and observing clotting. The results are presented in Table A

TABLE A

Testing of Sodium Starch Glycolate in heparinized blood

| Composition | Concentration (mg/mL) of Powder in Blood | 'Clotting' Time | Notes and observations |
|---|---|---|---|
| None - no additives to heparinized blood | NA | No clotting observed | |
| Sodium Starch Glycolate (Un-Oxidized) | 100 | No clotting observed | Formed chunks that broke into viscous liquid |
| Sodium Starch Glycolate - periodate oxidized combined | 50 | 10 min | Majority clotted at 8 min 41 s. |
| with CHES buffer as in | 75 | 5 min | |
| Example 1.4 (0.8 equivalents per starch AGU) | 100 | Instantly (within seconds) | |

As shown in Table A, Sodium Starch Glycolate-periodate oxidized with CHES buffer in a form of powder with added buffer exhibits very rapid clotting at 100 mg/ml.

Example 2. Hemostatic Patch with POSSG Powder

Powdered Periodate Oxidized Sodium Starch Glycolate, as described in the procedures of Example 1, particularly 1.2 and 1.4, was spread and loosely compressed on top of a substrate or matrix using spatula for further testing in hemostasis. The powder density on the substrate was 34±4 mg/cm$^2$.

Various substrates, including a CMC matrix, a knitted substrate with oxidized regenerated cellulose and a non-woven matrix having oxidized regenerated cellulose fibers, were combined with the POSSG material. For each application, the substrates were cut to 2 cm×3 cm in size. One or multi-layer of substrate was used that had a total thickness around 2 mm.

TABLE B

Testing of Substrates Forms and Materials

| | Substrate Description | Source | Patch Size | Thickness |
|---|---|---|---|---|
| CMC matrix | Non-woven fabric composed of carboxymethyl cellulose | Aquacel Wound dressing from Convatec Inc. | 2 cm × 3 cm | 2 mm |
| ORC Knitted Substrate | Knitted fabric composed of oxidized, regenerated cellulose | GYNECARE INTERCEED ® Absorbable Adhesion Barrier, available from Ethicon, Inc. | 2 cm × 3 cm | 2 mm (multi-layer) |
| ORC Non-Woven Matrix | Structured non-woven fabric, needle punched with interlocking oxidized, regenerated cellulose fibers | SURGICEL SNoW ™ Absorbable Hemostat, available from Ethicon, Inc. | 2 cm × 3 cm | 2 mm (multi-layer) |

The testing was performed in ex vivo models: 180° (Half) Anastomosis on a. Porcine Carotid Tissue; and b. 5 mm or 6 mm ePTFE graft.

The Half Anastomosis model was performed as follows. 180-degree single linear incision was created and repaired with appropriate suture and needle that gives a desired bleeding severity. Vessel was placed on the fixture so that the beginning and end are on the top and bottom during application. Blood was being pumped and circulating constantly through the vessel, mimicking clinically relevant blood flow under systolic/diastolic pressure. The blood used is bovine whole blood with added Na-Heparin that do not clot over time.

The hemostatic patch was then applied onto incision with added powder side facing the incision with 2 min tamponade and the bleeding was evaluated before and after application

TABLE C

Testing of hemostatic patches in ex vivo models at various blood pressure levels.

| Substrate/matrix | Pressure (mmHg) in Half Anastomosis models: porcine carotid tissue or ePTFE graft | Before, Leak Rate (g/min) | After, Leak Rate (g/min) | % Reduction in bleeding |
|---|---|---|---|---|
| CMC matrix (no powder added) | 80/40 | 4.02 | 3.10 | 23% |
| | 80/40 | 5.07 | 4.17 | 18% |
| | 120/80 | 4.90 | 4.35 | 11% |
| POSSG (no buffer) on the CMC matrix with a powder concentration 34 ± 4 $mg/cm^2$ | 80/40 | 5.10 | 4.99 | 2% |
| | 80/40 | 5.43 | 5.26 | 3% |
| | 80/40 | 4.55 | 4.32 | 5% |
| POSSG with a Bicarbonate buffer on the CMC matrix with powder concentration at 34 ± 4 $mg/cm^2$ with sodium bicarbonate at 0.87 equivalents per starch AGU. | 60/40 | 4.70 | 0.52 | 87% |
| | 80/40 | 4.34 | 2.60 | 40% |
| Periodate Oxidized Sodium Starch Glycolate with CHES buffer on CMC matrix with powder concentration at 34 ± 4 $mg/cm^2$. CHES is 0.17 equiv. over starch AGU. (LOW CHES) | 60/40 | 5.01 | 2.95 | 41% |
| | 60/40 | 6.75 | 3.94 | 42% |
| POSSG with a CHES buffer on the CMC matrix, powder concentration 34 ± 4 $mg/cm^2$ with 0.81 equivalents of CHES per starch AGU. (High CHES) | 40/NA | 0.88 | 0 | 100% |
| | 80/40 | 3.60 | 0 | 100% |
| | 120/80 | 3.32 | 0.50 | 85% |
| | 153/113 | 6.00 | 0.20 | 97% |
| | 80/40 (ePTFE graft) | 3.26 | 0 | 100% |
| | 80/40 (ePTFE graft) | 3.51 | 0 | 100% |

As shown in Table C, POSSG with greater CHES buffer on CMC matrix performed particularly well, with 100% reduction in bleeding rates on porcine carotid tissue at lower blood pressures, 85-97% reduction in bleeding rates on porcine carotid tissue at higher blood pressures, and 100% reduction in bleeding rates on ePTFE grafts.

Example 3. Comparison of Substrates with POSSG with CHES Buffer

Similarly to the Example 2, further testing was performed of various substrates performance with POSSG with CHES buffer. Powders were dosed on substrates at 34±4 $mg/cm^2$ density for each application. The results are presented in Table D.

TABLE D

Tests in ex vivo models at various blood pressure levels.

| Substrate/matrix | Pressure (mmHg) in Half Anastomosis models: porcine carotid tissue or ePTFE graft | Before, Leak Rate (g/min) | After, Leak Rate (g/min) | % Reduction in bleeding |
|---|---|---|---|---|
| POSSG with CHES Buffer on Knitted ORC Matrix | 50/NA | 5.24 | 0.43 | 92% |
| | 60/30 | 5.97 | 1.41 | 76% |
| | 60/30 | 6.44 | 1.42 | 78% |
| | 80/40 | 3.72 | 1.61 | 57% |
| | 120/80 | 3.12 | 1.95 | 38% |
| POSSG with CHES Buffer on Non-Woven ORC Matrix | 60/30 | 6.06 | 1.06 | 83% |
| | 120/80 | 4.71 | 2.32 | 51% |
| | 120/80 | 4.85 | 2.29 | 53% |

As shown in Table D in comparison to the results in Table C, the POSSG with a CHES Buffer on CMC matrix performed particularly well, with 100% reduction in bleeding rates on porcine carotid tissue at lower blood pressures, 85-97% reduction in bleeding rates on porcine carotid tissue at higher blood pressures, and 100% reduction in bleeding rates on ePTFE grafts.

TABLE E

| Porcine Carotid Tissue (An Anastomotic Bleeding Model) | | | | |
|---|---|---|---|---|
| Substrate/matrix | Pressure (mmHg) | Before, Leak Rate (g/min) | After, Leak Rate (g/min) | % Reduction in bleeding |
| Knitted ORC Matrix | 20/NA | 7.12 | 6.08 | 15% |
| (No POSSG Added) | 60/30 | 6.42 | 5.42 | 16% |
| | 80/40 | 5.66 | 5.00 | 12% |
| | 120/80 | 4.49 | 4.04 | 10% |
| Non-Woven ORC | 60/30 | 5.87 | 6.34 | — |
| Matrix (No POSSG | 60/30 | 6.04 | 2.69 | 55% |
| added) | 160/105 | 6.11 | 4.60 | 25% |

The data presented in the above Examples show improved performance in various hemostatic models of with the POSSG with a CHES buffer, in a powder form, and particularly when applied onto a CMC substrate. In some tests, POSSG with a CHES buffer, also performed acceptably well on knitted and non-woven, felt substrates.

We claim:

1. A flowable, tissue-adhesive powder comprising:

i. Oxidized crosslinked polysaccharides in powder form, such polysaccharides having a plurality of anhydroglucose units, wherein at least a portion of the anhydroglucose units have been oxidized to form aldehydes, and ii. 2-(cyclohexylamino) ethanesulfonate (CHES) as a zwitteronic buffer in lyophilizate form.

2. The flowable, tissue-adhesive powder according to claim 1, wherein the crosslinked polysaccharide is selected from the group consisting of starch glycolate, carboxy methyl cellulose, and combinations thereof.

3. The flowable powder according to claim 1, wherein the polysaccharides are crosslinked via reaction with a phosphate-containing compound.

4. The flowable powder according to claim 1, wherein the crosslinked polysaccharide is a sodium salt of carboxy methyl starch.

5. The flowable powder according to claim 1, wherein the crosslinked polysaccharide is starch glycolate.

6. The flowable powder according to claim 1, wherein each crosslinked polysaccharide has a plurality of aldehyde groups that have been formed via an oxidation reaction using a salt form of periodate.

* * * * *